US012576052B2

(12) United States Patent
Wang et al.

(10) Patent No.: US 12,576,052 B2
(45) Date of Patent: Mar. 17, 2026

(54) METFORMIN INHALATION POWDER AEROSOL FOR TREATING IDIOPATHIC PULMONARY FIBROSIS AND PREPARATION METHOD THEREOF

(71) Applicants: Wenzhou Medical University, Wenzhou (CN); Suzhou Inhal Pharma Co., Ltd., Suzhou (CN)

(72) Inventors: Fangyan Wang, Wenzhou (CN); Xiujie Liu, Wenzhou (CN); Zhengyang Song, Wenzhou (CN); Xiawei Ji, Wenzhou (CN); Hang Zhou, Ningbo (CN); Qingzhen Zhang, Suzhou (CN); Jie Dong, Ningbo (CN); Kaiqi Shi, Ningbo (CN)

(73) Assignees: Wenzhou Medical University, Wenzhou (CN); Suzhou Inhal Pharma Co., Ltd., Suzhou (CN)

( * ) Notice: Subject to any disclaimer, the term of this patent is extended or adjusted under 35 U.S.C. 154(b) by 332 days.

(21) Appl. No.: 18/361,242

(22) Filed: Jul. 28, 2023

(65) Prior Publication Data

US 2024/0041800 A1 Feb. 8, 2024

(30) Foreign Application Priority Data

Aug. 2, 2022 (CN) .......................... 202210922746.2

(51) Int. Cl.
| | |
|---|---|
| *A61K 9/00* | (2006.01) |
| *A61K 31/155* | (2006.01) |
| *A61K 47/26* | (2006.01) |
| *A61M 15/00* | (2006.01) |
| *A61P 11/00* | (2006.01) |

(52) U.S. Cl.
CPC .......... *A61K 31/155* (2013.01); *A61K 9/0075* (2013.01); *A61K 47/26* (2013.01); *A61M 15/0008* (2014.02); *A61P 11/00* (2018.01)

(58) Field of Classification Search
CPC .... A61K 31/155; A61K 9/0075; A61K 47/26; A61M 2202/064; A61M 11/003
See application file for complete search history.

(56) References Cited

U.S. PATENT DOCUMENTS

| | | | |
|---|---|---|---|
| 2006/0096595 A1* | 5/2006 | Nakamura ........ | A61M 15/0028 |
| | | | 128/203.19 |
| 2007/0215149 A1* | 9/2007 | King ................... | A61M 15/001 |
| | | | 128/200.24 |
| 2012/0071510 A1* | 3/2012 | Leone-Bay .......... | A61K 31/422 |
| | | | 514/415 |

OTHER PUBLICATIONS

Acosta et al (Inhalable Nanoparticles/Microparticles of an AMPK and Nrf2 Activator for Targeted Pulmonary Drug Delivery as Dry Powder Inhalers), The AAPS Journal (2021) 23:2, pp. 1-14. (Year: 2021).*

* cited by examiner

*Primary Examiner* — Mina Haghighatian
(74) *Attorney, Agent, or Firm* — Pilloff Passino & Cosenza LLP; Rachel Pilloff; Sean Passino

(57) ABSTRACT

Provided are a metformin inhalation powder aerosol for treating idiopathic pulmonary fibrosis and a preparation method thereof, including following steps: pretreating a metformin raw material to obtain fine powder, and passing the obtained fine powder through a screen with a mesh size of 100-1000 microns by an pendular granulator at a rotating speed of 200 revolutions per minute to obtain soft particle clusters; pre-spheronizing clusters at a vibration frequency of 100-300 hertz to obtain particle clusters, and then rolling the particle clusters on a granulating pan and spheronizing to obtain spherical particle clusters.

10 Claims, 9 Drawing Sheets

BLM

BLM+Met

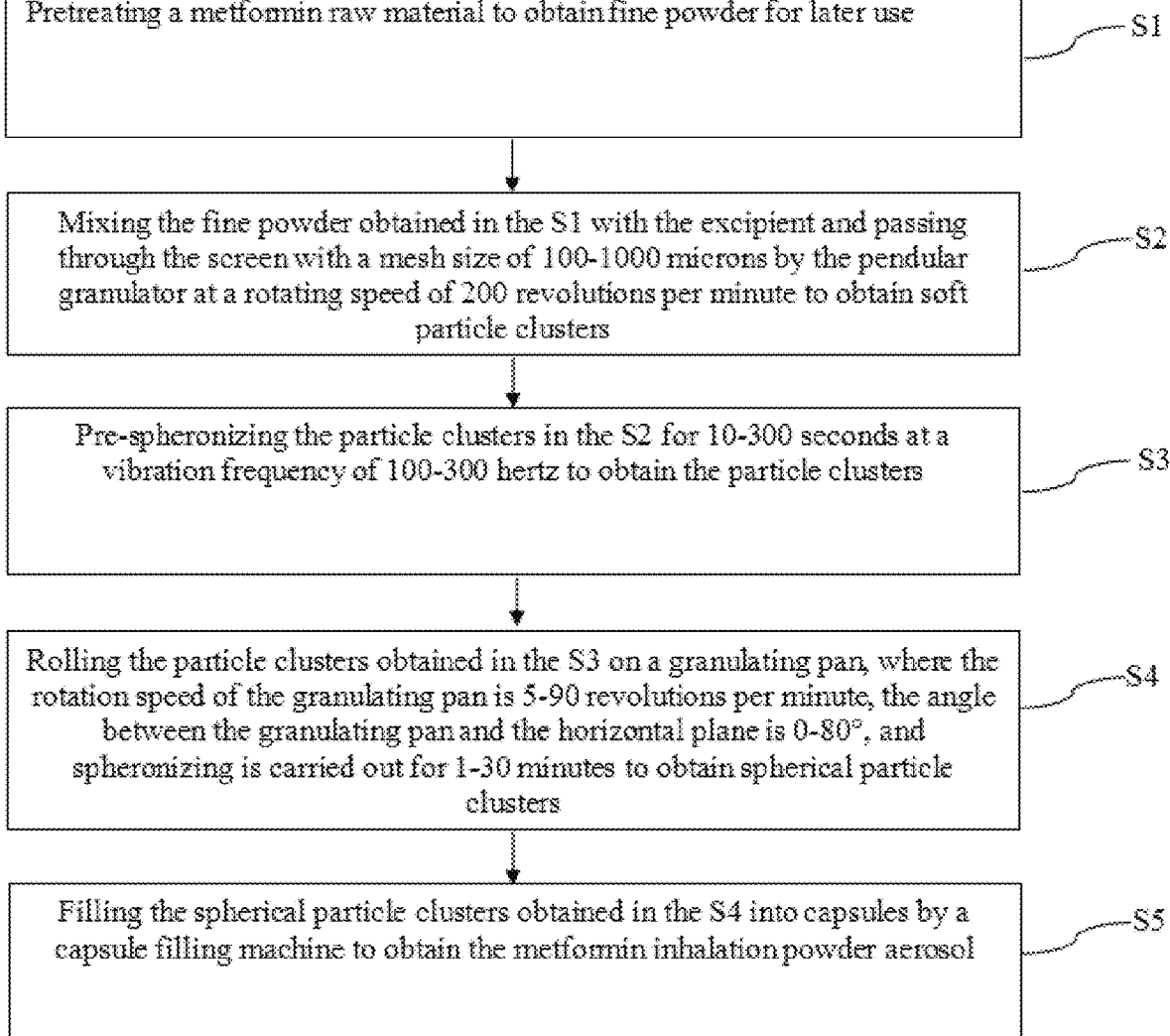

Pretreating a metformin raw material to obtain fine powder for later use —— S1

Mixing the fine powder obtained in the S1 with the excipient and passing through the screen with a mesh size of 100-1000 microns by the pendular granulator at a rotating speed of 200 revolutions per minute to obtain soft particle clusters —— S2

Pre-spheronizing the particle clusters in the S2 for 10-300 seconds at a vibration frequency of 100-300 hertz to obtain the particle clusters —— S3

Rolling the particle clusters obtained in the S3 on a granulating pan, where the rotation speed of the granulating pan is 5-90 revolutions per minute, the angle between the granulating pan and the horizontal plane is 0-80°, and spheronizing is carried out for 1-30 minutes to obtain spherical particle clusters —— S4

Filling the spherical particle clusters obtained in the S4 into capsules by a capsule filling machine to obtain the metformin inhalation powder aerosol —— S5

FIG. 8

METFORMIN INHALATION POWDER AEROSOL FOR TREATING IDIOPATHIC PULMONARY FIBROSIS AND PREPARATION METHOD THEREOF

CROSS-REFERENCE TO RELATED APPLICATIONS

This application claims priority of Chinese Patent Application No. 202210922746.2, filed on Aug. 2, 2022, the entire contents of which are incorporated herein by reference.

TECHNICAL FIELD

The application belongs to the field of treating idiopathic pulmonary fibrosis, and particularly relates to a metformin inhalation powder aerosol for treating idiopathic pulmonary fibrosis and a preparation method thereof.

BACKGROUND

Idiopathic Pulmonary Fibrosis (IPF) is a chronic, progressive and fibrotic interstitial lung disease with unclear etiology and pathogenesis. Lesions are mainly confined to the lungs, and middle-aged and elderly men are vulnerable to IPF. The lung histopathology of IPF and or chest high-resolution Computed Tomography (HRCT) are characterized by usual interstitial pneumonia (UIP). The clinical feature of IPF is progressive scar or fibrosis confined to the interstitial space of lung, which leads to the loss of lung function and eventually death. Symptoms of IPF include dry cough, fatigue dyspnea and fatigue. In the late stage of the disease, with decreased blood oxygen levels, the skin may appear blue staining (cyanosis), and the ends of fingers may become thicker or rod-shaped. With the progression of the disease, signs of pulmonary hypertension and right heart failure will also be observed.

At present, pirfenidone and nintedanib have been approved to treat IPF. Although they are able to slow down the progress of the disease, progressive fibrosis (scar) will eventually lead to death, and the median survival time of patients after diagnosis is only 3-5 years. Pifenidone developed by Intermune Company is a small molecule oral Collagen inhibitor and transforming growth factor-beta 1 (TGF-β1) inhibitor, which is used for treating IPF. On Oct. 16, 2008, pirfenidone was approved to be sold by Japan Pharmaceutical and Medical Device Agency (PMDA). The results of the ASCEND study in the New England Journal of Medicine (NEJM) show that pirfenidone can effectively slow down the disease progression of IPF patients after 52 weeks of treatment. The nintedanib is a small molecule chemical synthetic medicine developed by Boehringer-Ingelheim, which is a selective antagonist of vascular endothelial growth factor (VEGF), fibroblast growth factor (FGF) and platelet derived growth factor (PDGF) receptors. In October, 2014, US food and drug administration (FDA) approved the marketing of nintedanib esylate for the treatment of IPF.

It has been found in recent study that the imbalance of pulmonary flora may be an important pathogenesis of IPF, and metformin is able to play a variety of biological functions by regulating flora. Animal experiments show that inhalation of metformin is able to effectively alleviate the pathological damage of pulmonary fibrosis and reverse pulmonary fibrosis.

Inhalation administration has the advantages of quick onset, good curative effects, avoiding first-pass effect and reducing adverse reactions, especially suitable for lung diseases, and has become a kind of administration method that has attracted much attention. Dry powder inhalers refer to micronized drugs or preparations with carriers in the form of capsules, vesicles or multi-dose storage, in which patients actively inhale atomized drugs into the lungs and deposit them in the lungs to play a local or systemic role. Compared with conventional atomized inhalers and metered-dose inhalers, dry powder inhalers have the advantages of lightness, portability, convenience in use, and are more friendly to the ecological environment, thus becoming a very popular inhalation administration tool in clinic.

However, due to the high surface free energy of fine particles, especially those with a particle size less than 20 microns, these particles are usually easy to agglomerate together due to the van der Waals force between particles, and the bulk density of these agglomerates is very low, so they often show poor fluidity, which is not conducive to transportation and measurement. In inhalation preparations, it is often desirable that the particle size of the powder is in a very small scale but shows good fluidity and dispersibility. Therefore, it is usually necessary to add a large amount of dispersant such as lactose and mannitol, or add a third component such as mannitol, phospholipid, leucine, magnesium stearate and polyethylene glycol 6000 to improve the fluidity.

However, the above scheme has a limited effect on improving the fluidity of powder, and greatly limits the amount of active substances that can be added. Preparing powder into granules is an effective method to improve fluidity, and adding solution to powder for granulation or pressing powder into granules by pressure is a common method at present. However, these methods often make the powder irreversibly become large particles, which are impossible to be broken into fine particles by airflow, so they are not suitable for inhalation field.

SUMMARY

In order to solve the above technical problems, the application provides a metformin inhalation powder aerosol for treating idiopathic pulmonary fibrosis (IPF) and a preparation method thereof.

The technical scheme of the application is as follows.

A preparation method of a metformin inhalation powder aerosol for treating IPF includes the following steps:

S1, pretreating a metformin raw material to obtain fine powder for later use;

S2, passing the fine powder obtained in the S1 through a screen with a mesh size of 100-1000 microns by a pendular granulator at a rotating speed of 200 revolutions per minute to obtain soft particle clusters;

S3, pre-spheronizing the particle clusters in the S2 for 10-300 seconds at a vibration frequency of 100-300 hertz to obtain the particle clusters;

S4, rolling the particle clusters obtained in the S3 on a granulating pan, where the rotation speed of the granulating pan is 5-90 revolutions per minute, the angle between the granulating pan and the horizontal plane is 0-80°, and spheronizing is carried out for 1-30 minutes to obtain spherical particle clusters; and S5, filling the spherical particle clusters obtained in the S4 into capsules by a capsule filling machine to obtain the metformin inhalation powder aerosol.

Optionally, the metformin raw material is metformin or a metformin sodium.

Optionally, D90 in the fine powder is less than 5 microns.

Optionally, the S2 further includes excipient. The fine powder and the excipient are granulated by the oscillating granulator, and the excipient is lactose monohydrate and/or mannitol.

Optionally, the mass ratio of the metformin raw material to excipient is (10-100):(0-90).

Optionally, the D90 of the excipient is less than 30 microns.

Optionally, the dry powder inhaler for the metformin inhalation powder aerosol includes a dust-proof cover, a suction nozzle, a medicine bin, a bottom cover and two needling units. The suction nozzle, the medicine bin and the bottom cover are sequentially connected. A channel is arranged on the suction nozzle. The channel has a spiral channel structure, and a grid filter screen is arranged at the bottom of the channel. The dust-proof cover is arranged on the suction nozzle. The medicine bin is provided with a medicine storage bin for placing metformin inhalation powder aerosol. The left and right sides of the lower part of the medicine bin are provided with through holes communicated with the medicine storage bin.

The two needling units are symmetrically arranged on left and right sides of the lower part of the medicine bin, and each of needling units include a button, a steel needle, a needle seat and a spring. The needle seat is arranged on the inner side of the button, an end of the steel needle is arranged on the inner side of the needle seat, the other end of the steel needle extends into the corresponding one of through holes, and a spring is sleeved on the steel needle between the needle seat and the outer wall of the medicine bin.

The application also provides a metformin inhalation powder aerosol for treating IPF, which is prepared by the preparation method described above.

The application provides a metformin inhalation powder aerosol for treating IPF and a preparation method thereof. Compared with the conventional powder aerosol granulation process, spherical particles are able to be prepared without using solvents or adhesives, and the prepared particles have a certain strength to meet the needs of transportation and filling, and the particle size of spherical particle clusters is less than 1000 microns, so the fluidity is improved, and spherical particle clusters are able to be redispersed into fine particles under the action of airflow, thus having a good therapeutic effect on IPF.

4

Figure 1:
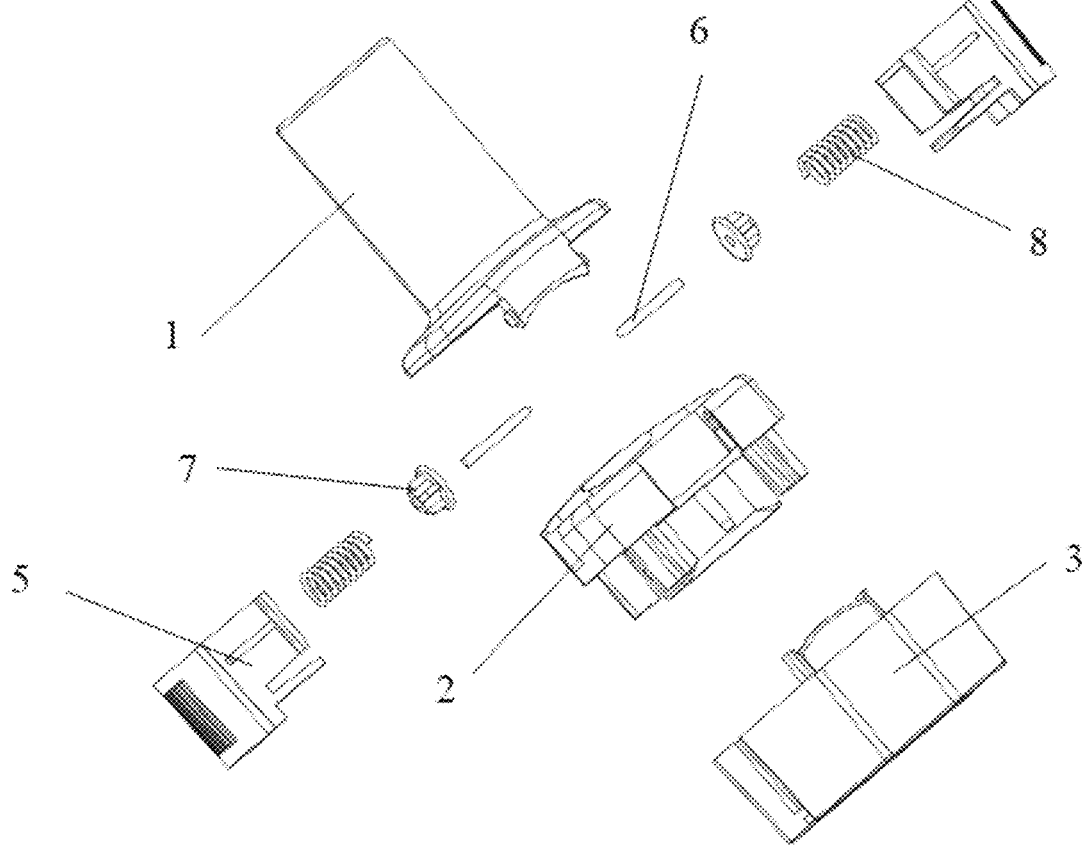
FIG. 1 is a schematic structural diagram of a dry powder inhaler used for metformin inhalation powder aerosol according to the present application.

FIG. 8 shows a process of a preparation method of a metformin inhalation powder aerosol for treating IPF according to the present application.

DETAILED DESCRIPTION OF THE EMBODIMENTS

As shown in FIG. 8, a preparation method of a metformin inhalation powder aerosol for treating IPF provided by the present application includes the following steps:

S1, pretreating a metformin raw material to obtain fine powder for later use;

S2, mixing the fine powder obtained in the S1 with the excipient and passing through the screen with a mesh size of 100-1000 microns by the pendular granulator at a rotating speed of 200 revolutions per minute to obtain soft particle clusters;

S3, pre-spheronizing the particle clusters in the S2 for 10-300 seconds at a vibration frequency of 100-300 hertz to obtain the particle clusters;

S4, rolling the particle clusters obtained in the S3 on a granulating pan, where the rotation speed of the granulating pan is 5-90 revolutions per minute, the angle between the granulating pan and the horizontal plane is 0-80°, and spheronizing is carried out for 1-30 minutes to obtain spherical particle clusters; and S5, filling the spherical particle clusters obtained in the S4 into capsules by a capsule filling machine to obtain the metformin inhalation powder aerosol.

Compared with the traditional powder aerosol granulation process, spherical particles are able to be prepared without using solvents or adhesives, and the prepared particles have a certain strength to meet the needs of transportation and filling, and the particle size of spherical particle clusters is less than 1000 microns, so the fluidity is improved, and spherical particle clusters are able to be redispersed into fine particles under the action of airflow.

In an embodiment, in the S1, the metformin raw material is metformin or a metformin sodium. The methods of pretreating of metformin raw material include but are not limited to jet milling, ball milling, spray drying and recrystallization, so that the D90 in the fine powder obtained after pretreatment of metformin raw material is less than 5 microns.

In the S2, the excipient may be lactose monohydrate or mannitol, which plays a role of increasing the fluidity and dispersibility of the prescription. The D90 in the excipient is less than 30 microns. In addition, when the pendular granulator is used for granulation, the mesh size of the screen is 100-1000 microns, preferably 200-500 microns.

It should be noted that the mass ratio of the metformin raw material to excipient is (10-100):(0-90).

In the S3, during pre-spheronizing, the vibration frequency is 100 hertz-300 hertz, preferably 100-250 hertz; the vibration time is 10-300 seconds, preferably 30-120 seconds.

In the S4, during spheronizing, the rotating speed of the granulating pan is 5-90 revolutions per minute, preferably 30-60 revolutions per minute. The angle between the granulating pan and the horizontal plane is 0-80°, preferably 30-50°. The pre-spheronizing time is 1-30 minutes, preferably 3-15 minutes.

Figure 2:
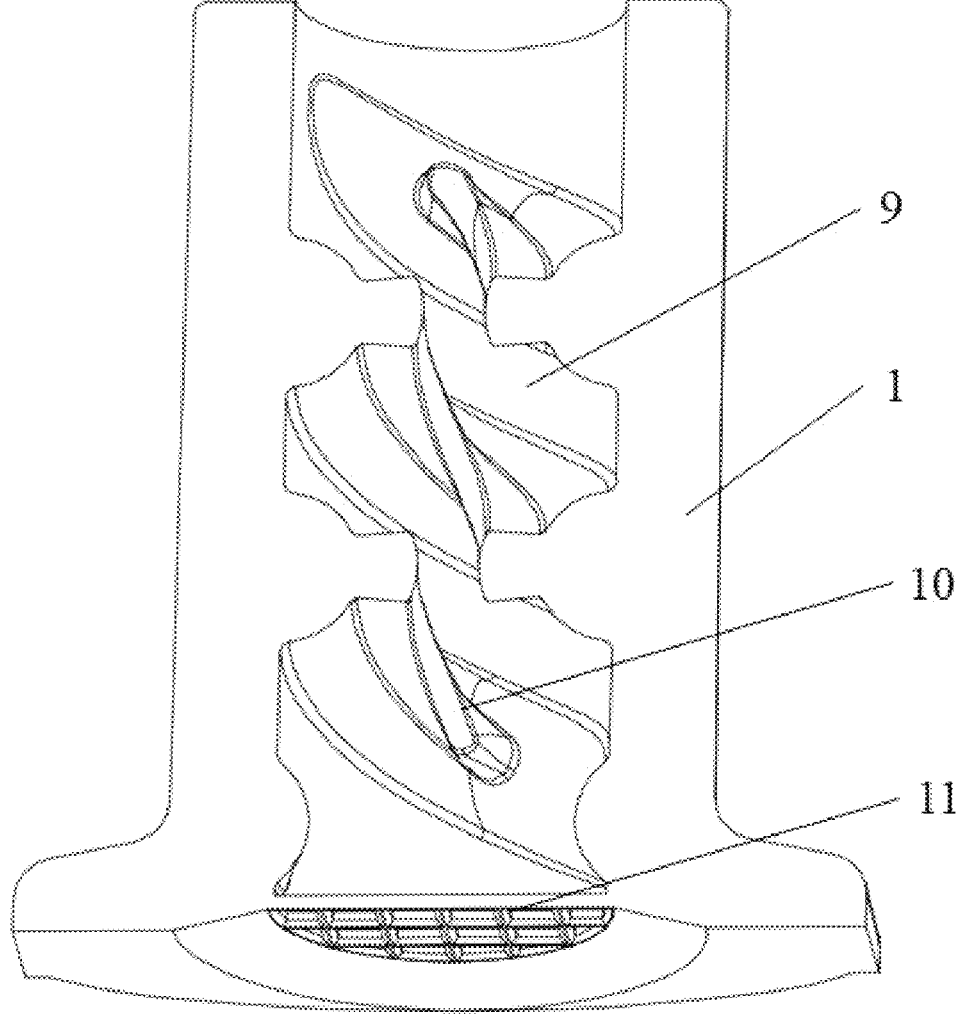
FIG. 2 is a schematic structural view of a suction nozzle in FIG. 1.

In order to improve the delivery dose of spherical particle clusters and the proportion of fine particles in metformin inhalation powder aerosol, referring to FIG. 1-FIG. 2, the dry powder inhaler used for metformin inhalation powder aerosol includes a dust-proof cover, a suction nozzle 1, a medicine bin 2, a bottom cover 3 and two needling units 4. The suction nozzle 1, the medicine bin 2 and the bottom cover 3 are connected in sequence. The suction nozzle 1 is provided with a channel. The channel has a spiral channel structure, and the bottom of the channel is provided with a grid filter screen 11. The suction nozzle 1 is provided with the dust-proof cover. The medicine bin 2 is provided with a medicine storage bin for placing metformin inhalation powder aerosol. The left and right sides of the lower part of the medicine bin 2 are provided with through holes communicated with the medicine storage bin. The two needling units 4 are symmetrically arranged on left and right sides of the lower part of the medicine bin 2, and each of the needling units 4 include a button 5, a steel needle 6, a needle seat 7 and a spring 8. The needle seat 7 is arranged inside the button 5, and an end of the steel needle 6 is arranged inside the needle seat 7, and the other end of the steel needle 6 extends into the through holes, and a spring 8 is sleeved on the steel needle 6 between the needle seat 7 and the outer wall of the medicine bin 2. When in use, the medicine bin 2 is opened, the metformin inhalation powder aerosol is placed in the medicine storage bin, the medicine bin 2 is closed and the button 5 is pressed, and the button 5 ejects the needle to puncture the capsules. When inhaling, the airflow enters from two centrally symmetrical flow channels to form a rotating airflow, which takes the medicine powder out of the capsules and makes the medicine powder enter the spiral channel in the suction nozzle 1. The capsules will be taken out of the confined bin by airflow when inhaling, and rotate above the confined bin along with the airflow direction.

The dry powder inhaler of the application is improved on the basis of Breezhaler. metformin raw material is prepared into inhalable spherical particle clusters and are matched with the dry powder inhaler to treat IPF, so that a high proportion of fine particles is achieved while low resistance is ensured and the lung deposition rate is guaranteed. The interior of the suction nozzle 1 of the application is a spiral channel with a layer of grid filter screen 11, that is, it has both grid and spiral flow channels, and the proportion of fine particles FPF (fine particle fraction) is as high as over 70%, which has a better effect on treating IPF.

It should be noted that the suction nozzle 1 only with a spiral flow channel or only with a grid flow channel has the proportion of fine particles FPF about 50%, which is lower than the effect of the dry powder inhaler of the present application.

In addition, in order not to rupture the capsule shell, the needle tip of the steel needle 6 includes three faces. In other words, the needle tip is a triangular pyramid, so that the steel needle 6 is able to form a small hole for medicine to enter and exit when puncturing the capsules, and the capsule shell does not rupture.

In the application, in order to realize a higher proportion of fine particles while low resistance is ensured, the channel is a double spiral channel. The double spiral channel preferably includes fan-shaped rotating ribs 10 and rectangular spiral ribs 9 which surround the inner wall of the channel at intervals.

The application also provides a metformin inhalation powder aerosol for treating IPF, including the metformin inhalation powder aerosol prepared by the preparation method describe above.

The powder aerosol prepared by the application is inhaled by the dry powder inhaler, which has the advantages of quick efficacy and good curative effect, reduces adverse reactions at the same time, is able to avoid the first-pass effect, and is especially suitable for lung diseases. The raw materials of the application are easily available and cheap. The spherical particles are able to be prepared without excipient, with excellent fluidity and low resistance, and excellent dispersion effect is able to be obtained under low resistance with the help of double spiral channel.

In order to further illustrate the present application, a metformin inhalation powder aerosol for treating IPF provided by the present application and its preparation method are described in detail with embodiments, but they cannot be understood as limiting the protection scope of the present application.

Embodiment 1

The dry powder inhaler includes the dust-proof cover, the suction nozzle 1, the medicine bin 2, the bottom cover 3 and two needling units 4. The suction nozzle 1, the medicine bin 2 and the bottom cover 3 are connected in sequence. The suction nozzle 1 is provided with the channel. The channel has a double spiral channel structure, and the double spiral channel consists of a fan-shaped rotating ribs 10 and rectangular spiral ribs 9. The fan-shaped rotating ribs 10 and rectangular spiral ribs 9 surround the inner wall of the channel at intervals, and the bottom of the channel is provided with a grid filter screen 11. The suction nozzle 1 is provided with a dust-proof cover. The medicine bin 2 is provided with the medicine storage bin for placing metformin inhalation powder aerosol. The left and right sides of the lower part of the medicine bin 2 are provided with through holes communicated with the medicine storage bin.

The two needling units 4 are symmetrically arranged on left and right sides of the lower part of the medicine bin 2, and each of the needling units include the button 5, the steel needle 6, the needle seat 7 and the spring 8. The needle seat 7 is arranged on the inner side of the button 5, and an end of steel needle 6 is arranged on the inner side of the needle seat 7. The needle tip of the steel needle 6 is a triangular pyramid, and the other end of the steel needle 6 extends into the corresponding one of through holes. The spring 8 is sleeved on the steel needle 6 between the needle seat 7 and the outer wall of the medicine bin 2.

Embodiment 2

A preparation method of a metformin inhalation powder aerosol for treating IPF provided by the present application includes the following steps:

S1, pretreating metformin to obtain fine powder with the particle size of D90<5 microns for later use;

S2, passing the fine powder obtained in the S1 through the screen with a mesh size of 300 microns by the pendular granulator at a rotating speed of 200 revolutions per minute to obtain soft particle clusters;

S3, pre-spheronizing the particle clusters in the S2 for 80 seconds at a vibration frequency of 200 hertz to obtain the particle clusters;

S4, rolling the particle clusters obtained in the S3 on a granulating pan, where the rotation speed of the granulating pan is 40 revolutions per minute, the angle between the granulating pan and the horizontal plane is 40°, and spheronizing is carried out for 10 minutes to obtain spherical particle clusters; and S5, filling the spherical particle clusters obtained in the S4 into capsules by a capsule filling machine to obtain the metformin inhalation powder aerosol.

7

Embodiment 3

A preparation method of a metformin inhalation powder aerosol for treating IPF provided by the present application includes the following steps:

S1, pretreating metformin to obtain fine powder with the particle size of D90<5 microns for later use;

S2, passing the fine powder obtained in the S1 and lactose monohydrate with a particle size of D90<30 microns through the screen with a mesh size of 100 microns by the pendular granulator at a rotating speed of 200 revolutions per minute to obtain soft particle clusters, where the mass ratio of metformin raw material to lactose monohydrate is 1:9;

S3, pre-spheronizing the particle clusters in the S2 for 300 seconds at a vibration frequency of 10 hertz to obtain the particle clusters;

S4, rolling the particle clusters obtained in the S3 on a granulating pan, where the rotation speed of the granulating pan is 5 revolutions per minute, the angle between the granulating pan and the horizontal plane is 80°, and spheronizing is carried out for 30 minutes to obtain spherical particle clusters; and S5, filling the spherical particle clusters obtained in the S4 into capsules by a capsule filling machine to obtain the metformin inhalation powder aerosol.

Embodiment 4

A preparation method of a metformin inhalation powder aerosol for treating IPF provided by the present application includes the following steps:

S1, pretreating metformin raw material to obtain fine powder with the particle size of D90<5 microns for later use;

S2, passing the fine powder obtained in the S1 and mannitol with a particle size of D90<30 microns through the screen with a mesh size of 1000 microns by the pendular granulator at a rotating speed of 200 revolutions per minute to obtain soft particle clusters, where the mass ratio of metformin to mannitol is 1:1;

S3, pre-spheronizing the particle clusters in the S2 for 10 seconds at a vibration frequency of 300 hertz to obtain the particle clusters;

S4, rolling the particle clusters obtained in the S3 on a granulating pan, where the rotation speed of the granulating pan is 90 revolutions per minute, the angle between the granulating pan and the horizontal plane is 0°, and spheronizing is carried out for 1 minute to obtain spherical particle clusters; and S5, filling the spherical particle clusters obtained in the S4 into capsules by a capsule filling machine to obtain the metformin inhalation powder aerosol.

Embodiment 5

A preparation method of a metformin inhalation powder aerosol for treating IPF provided by the present application includes the following steps:

S1, pretreating metformin hydrochloride to obtain fine powder with the particle size of D90<5 microns for later use;

S2, passing the fine powder obtained in the S1 through the screen with a mesh size of 200 microns by the pendular granulator at a rotating speed of 200 revolutions per minute to obtain soft particle clusters;

S3, pre-spheronizing the particle clusters in the S2 for 120 seconds at a vibration frequency of 100 hertz to obtain the particle clusters;

S4, rolling the particle clusters obtained in the S3 on a granulating pan, where the rotation speed of the granulating pan is 30 revolutions per minute, the angle between the granulating pan and the horizontal plane is 50°, and spheronizing is carried out for 15 minutes to obtain spherical particle clusters; and S5, filling the spherical particle clusters obtained in the S4 into capsules by a capsule filling machine to obtain the metformin inhalation powder aerosol.

Embodiment 6

A preparation method of a metformin inhalation powder aerosol for treating IPF provided by the present application includes the following steps:

S1, pretreating metformin hydrochloride to obtain fine powder with the particle size of D90<5 microns for later use;

S2, passing the fine powder obtained in the S1 and lactose monohydrate with a particle size of D90<30 microns through the screen with a mesh size of 500 microns by the pendular granulator at a rotating speed of 200 revolutions per minute to obtain soft particle clusters, where the mass ratio of metformin raw material to lactose monohydrate is 7:3;

S3, pre-spheronizing the particle clusters in the S2 for 30 seconds at a vibration frequency of 250 hertz to obtain the particle clusters;

S4, rolling the particle clusters obtained in the S3 on a granulating pan, where the rotation speed of the granulating pan is 60 revolutions per minute, the angle between the granulating pan and the horizontal plane is 30°, and spheronizing is carried out for 3 minutes to obtain spherical particle clusters; and S5, filling the spherical particle clusters obtained in the S4 into capsules by a capsule filling machine to obtain the metformin inhalation powder aerosol.

Comparative Example 1

Figure 3:
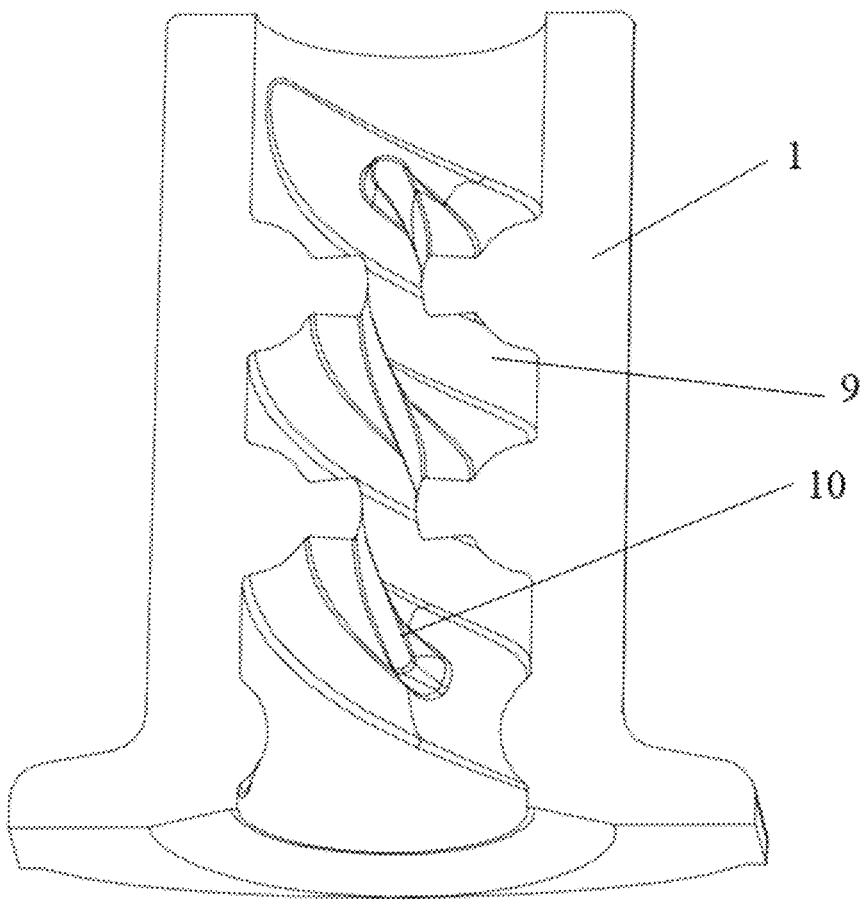
FIG. 3 is a schematic structural view of a suction nozzle of Comparative Example 1.

The only difference from Embodiment 1 is that the suction nozzle 1 is provided with a channel. The channel is a double spiral channel, and the double spiral channel includes fan-shaped rotating ribs 10 and rectangular spiral ribs 9. The fan-shaped rotating ribs 10 and rectangular spiral ribs 9 surround the inner wall of the channel at intervals, and the bottom of the channel is not provided with a grid filter screen 11, see FIG. 3 for details.

Comparative Example 2

Figure 4:
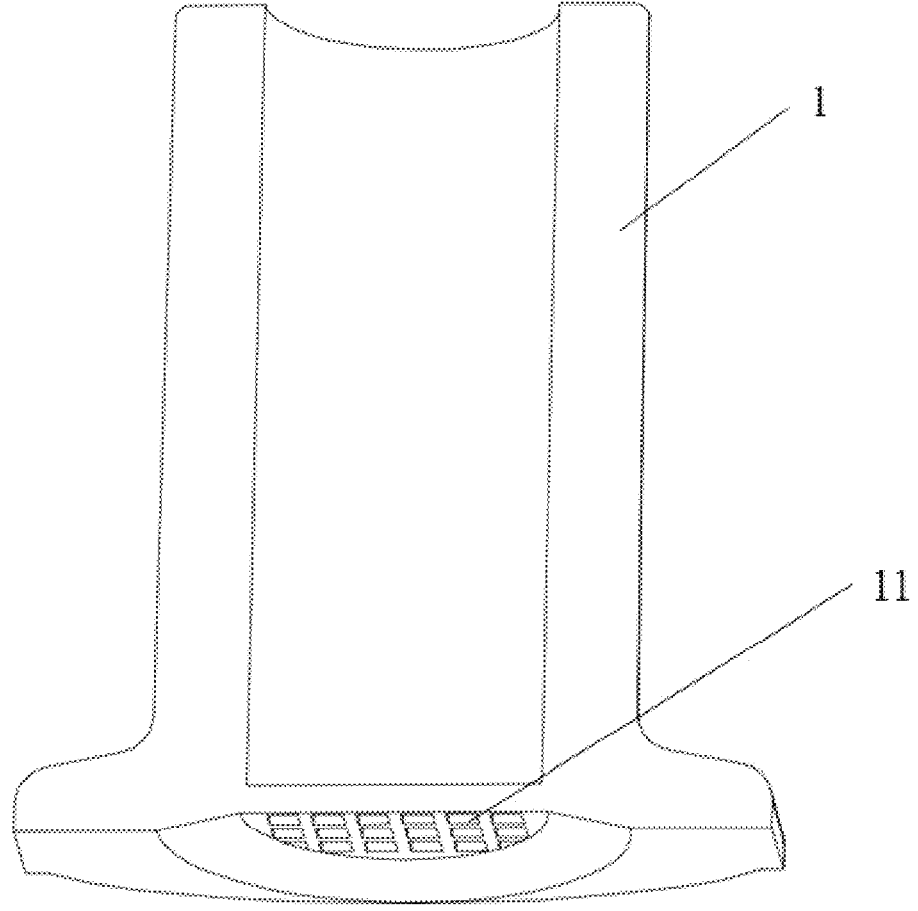
FIG. 4 is a structural schematic diagram of a suction nozzle of comparative example 2.

The only difference from Embodiment 1 is that the suction nozzle 1 is provided with a channel, and the bottom of the channel is provided with a grid filter screen 11, see FIG. 4 for details.

Comparative Example 3

The only difference from Embodiment 3 is that metformin is pretreated to obtain fine powder with a particle size of D90≥5 microns, and the rest are completely the same as Embodiment 3.

Comparative Example 4

The only difference from Embodiment 3 is that the particle size of lactose monohydrate is D90≥30 microns, and the rest are completely the same as Embodiment 3.

Comparative Example 5

The only difference from Embodiment 2 is that there is no S2, and the rest are exactly the same as Embodiment 2.

Comparative Example 6

The only difference from Embodiment 2 is that there is no S3, and the rest are exactly the same as Embodiment 2.

Comparative Example 7

The only difference from Embodiment 2 is that there is no S4, and the rest are exactly the same as Embodiment 2.

1. FPF Determination

The FPF of powder aerosol prepared in Embodiments 2-5 was measured by using the dry powder inhalers of Embodiment 1 and Comparative Examples 1-2 respectively according to the method for determining aerodynamic characteristics of fine particles of inhalation preparations in China Pharmacopoeia 2020 (Appendix 0951), and the results are shown in Table 1.

Among them, experimental groups 1-4 shows determination of embodiments 2-5 which are measured by dry powder inhaler of embodiment 1 respectively.

Control groups 1-2 shows determination of embodiment 3, which is measured by dry powder inhaler of embodiment 1.

Control groups 3-4 shows determination of comparative examples 3-4, which are measured by dry powder inhalers of Embodiment 1 respectively.

is as high as more than 70%. Therefore, the dry powder inhaler of the application is able to achieve better effect in the process of medicine deposition in the lungs.

In addition, the spherical particle clusters of the metformin inhalation powder aerosol obtained by the preparation method of the application have high amount of fine particles FPF.

2. Determination of Particle Size Distribution

According to China Pharmacopoeia 2020, the particle size distribution of spherical particle clusters in Embodiment 2 and Comparative Examples 5-7 is determined by screening method, and the results are shown in Table 2.

TABLE 2

| Determination Results of Particle Size Distribution | | | | |
| --- | --- | --- | --- | --- |
| Particle Size/microns | Embodiment 2 | Comparative Example 5 | Comparative Example 6 | Comparative Example 7 |
| <100 | 0.95 ± 0.08 | 0.78 ± 0.11 | 1.13 ± 0.06 | 0.95 ± 0.08 |
| 100-200 | 6.03 ± 0.11 | 4.12 ± 0.22 | 5.13 ± 0.15 | 13.36 ± 1.33 |
| 200-300 | 23.01 ± 2.21 | 6.27 ± 0.54 | 7.89 ± 0.62 | 20.12 ± 1.41 |
| 300-400 | 22.13 ± 0.98 | 14.29 ± 1.82 | 15.14 ± 0.74 | 55.14 ± 3.38 |
| 400-500 | 45.81 ± 3.45 | 15.36 ± 2.89 | 21.44 ± 1.99 | 10.35 ± 1.25 |
| 500-600 | 2.05 ± 0.09 | 23.13 ± 4.13 | 31.98 ± 3.32 | 0.05 ± 0.01 |
| >600 | 0.02 ± 0.02 | 35.51 ± 9.25 | 17.29 ± 1.82 | 0.03 ± 0.01 |
| Bulk density g/cm$^3$ | 0.34 ± 0.04 | 0.29 ± 0.05 | 0.32 ± 0.04 | 0.28 ± 0.03 |

As can be seen from Table 2, the bulk density of spherical particle clusters in the metformin inhalation powder aerosol prepared by the preparation method of the present application is larger than that in Comparative Examples 5-7.

3. Animal Experiments

Establishment of pulmonary fibrosis model: C57BL6 mice aged 6-8 weeks are selected and adapted for one week.

TABLE 1

| | Embodiment 2 | Embodiment 3 | Embodiment 4 | Embodiment 5 | Control group 1 | Control group 2 | Control group 3 | Control group 4 |
| --- | --- | --- | --- | --- | --- | --- | --- | --- |
| Induction Port + adapter | 3193.51 | 293.59 | 1277.41 | 1916.11 | 440.39 | 654.12 | 1163.18 | 267.17 |
| Preseparator | 887.03 | 87.08 | 372.55 | 629.79 | 139.32 | 247.68 | 325.37 | 95.78 |
| Stage 1 | 139.83 | 19.72 | 55.93 | 88.09 | 22.68 | 24.11 | 23.58 | 18.74 |
| Stage 2 | 1220.01 | 120.09 | 500.21 | 915.01 | 132.10 | 170.37 | 60.38 | 106.88 |
| Stage 3 | 3995.13 | 395.13 | 1757.86 | 2916.45 | 276.59 | 336.89 | 159.67 | 391.18 |
| Stage 4 | 5163.14 | 597.27 | 2220.15 | 3459.30 | 418.09 | 344.57 | 165.39 | 501.02 |
| Stage 5 | 3131.76 | 330.36 | 1377.98 | 2348.82 | 231.25 | 237.14 | 86.35 | 343.58 |
| Stage 6 | 982.34 | 82.73 | 402.76 | 658.17 | 58.74 | 84.15 | 34.27 | 79.42 |
| Stage 7 | 199.11 | 19.61 | 87.61 | 139.38 | 14.90 | 20.34 | 5.36 | 17.84 |
| Micro Orifice Collector | 27.63 | 3.13 | 11.88 | 17.41 | 2.76 | 3.31 | 1.59 | 2.79 |
| Sum/μg | 18939.49 | 1948.71 | 8064.32 | 13088.52 | 1736.82 | 2122.68 | 2025.14 | 1824.40 |
| FPF/% | 71.32 | 74.97 | 72.24 | 71.99 | 60.73 | 47.84 | 22.36 | 72.85 |

As can be seen from Table 1, the amount of fine particles FPF is about 50% in the flow channel only with double spiral and the flow channel only with grid filter screen. The application has both a grid filter screen and a spiral flow channel, and after testing, the amount of fine particles FPF Bleomycin (3 mg/kg/50 μl) is given orally to mice in BLM group and BLM+Met group on the first day, and the dry powder of bleomycin is prepared to the required concentration with sterile phosphate buffer saline non-surgical method of bleomycin orally injected into mice's lungs: mice are anesthetized with isoflurane and hung on the operating board at 70°. Bleomycin is dripped orally using a 200 μl pipette).

Among them, BLM: bleomycin-induced pulmonary fibrosis mouse model group; BLM+Met: the effect of atomization inhalation of metformin on macroscopic damage of lung in mice with pulmonary fibrosis. This group is treated by atomization inhalation of metformin inhalation powder aerosol in Embodiment 2 with dry powder inhaler: **P<0.01, n=10.

Dosage of inhaled metformin: the reference value of local administration concentration of metformin in upper respiratory tract is 200 mg/kg. According to the weight of 25 g per mouse, each mouse inhales 5 mg of metformin inhalation powder aerosol in Embodiment 2 every day for 3 weeks.

Weighing: weights of the mice are weighed at a fixed time every morning and recorded, and the changes of mice's weight are observed at different times in each group.

Hematoxylin Eosin (HE) staining and Masson staining: the lung tissue of mice is fixed in 4% paraformaldehyde for 24 hours, washed overnight with running water, dehydrated by conventional alcohol, embedded in paraffin, cut into 5-micron slides, stained with HE and Masson, and sealed with neutral gum after applying xylene for transparency. The pathological changes of lung are observed under optical microscope and photos are taken.

α-SMA immunofluorescence: lung tissue slides are dried at 65° C., dewaxed with xylene and dehydrated with gradient alcohol. Washing with PBS for 3 times, each time for 10 minutes, and the liquid around the slides is wiped with filter paper to avoid damaging the tissue on the slides. 0.1% TritonX-100 (prepared by PBS) is added dropwise to the glass slides, and the film was permeabilized at room temperature for 30 minutes. PBS washing is carried out for 3 times, each time for 10 minutes. Sealing with 5% BSA (PBS) is carried out for 30 minutes and no washing. Primary antibodies (α-SMA, 1:100) prepared in advance from different species is added, and incubation overnight is done at 4° C. PBS washing is carried out for 3 times, each time for 10 minutes. In the dark environment, the fluorescent labeled secondary antibodies of the corresponding species (all diluted at 1:200) are added and incubated at room temperature for 1 hour. PBS washing is carried out for 3 times, each time for 10 minutes. DAPI staining and incubation at room temperature for 5 minutes are carried out. PBS washing is carried out for 3 times, each time for 3 minutes. The slides are sealed and the fluorescence intensity is observed under a fluorescence microscope.

Statistical analysis: the experimental data of each group are statistically analyzed by GraphpadPrism9.0 software. All the experimental data are tested for normality, and the measurement data are expressed as mean±standard deviation. The mean of multiple groups of samples is compared by One-way Analysis of Variance (one-way ANOVA). $P<0.05$ is statistically significant. The results are shown in FIG. 5A, FIG. 5B, FIG. 6 and FIG. 7.

Figure 5A:
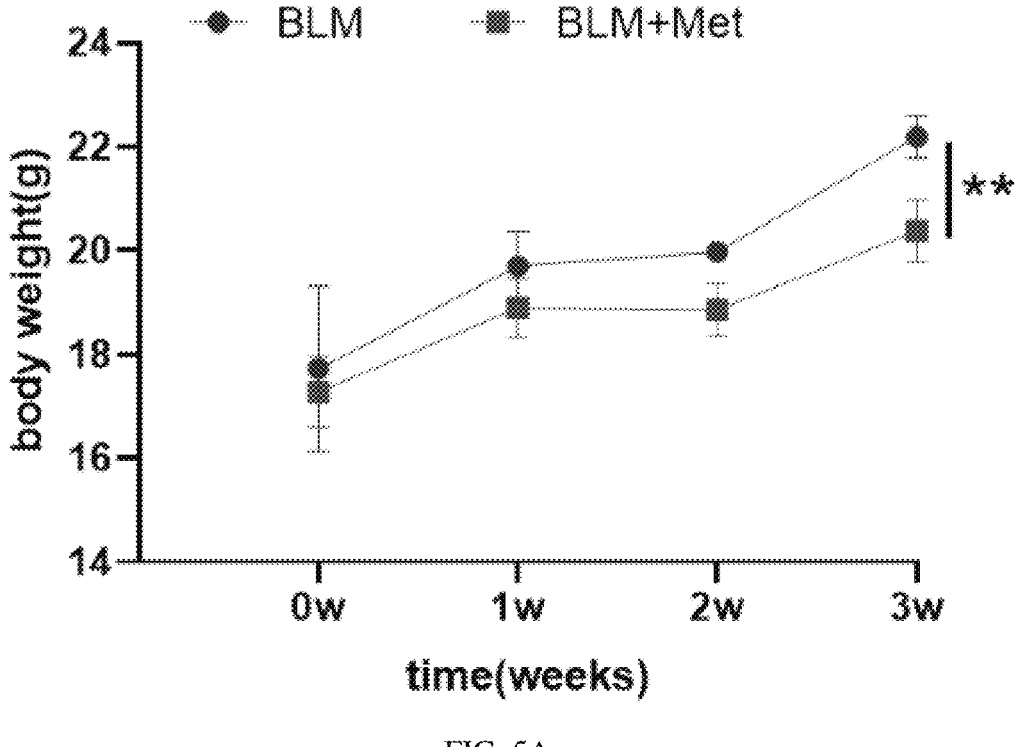
FIG. 5A shows an effect of atomized inhalation of metformin on a body weight of mice with pulmonary fibrosis.
Figure 5B:
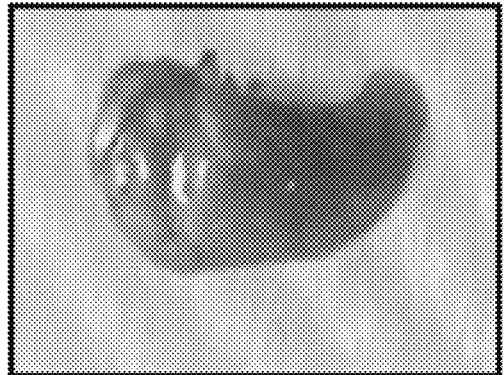
FIG. 5B shows an effect of atomized inhalation of metformin on macroscopic damage of lung in mice with pulmonary fibrosis.
Figure 5B:
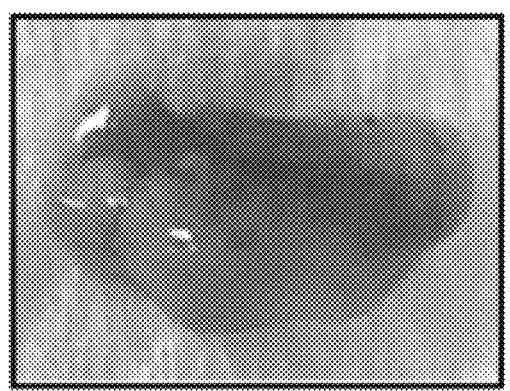

1) Metformin is Able to Reduce the Body Weight and Macroscopic Damage of Pulmonary Fibrosis in Mice FIG. 5A shows that compared with BLM group, the weight of BLM+Met group is decreased and the difference between them was more significant with the increase of time. FIG. 5B shows that in BLM group, the lung moistening degree is decreased, the lung tissue is congested and edema, and the color is dark and uneven. The lung in BLM+Met group is pink, with smooth surface and elastic touch, which shows significant pathological changes compared with BLM group.

Figure 6:
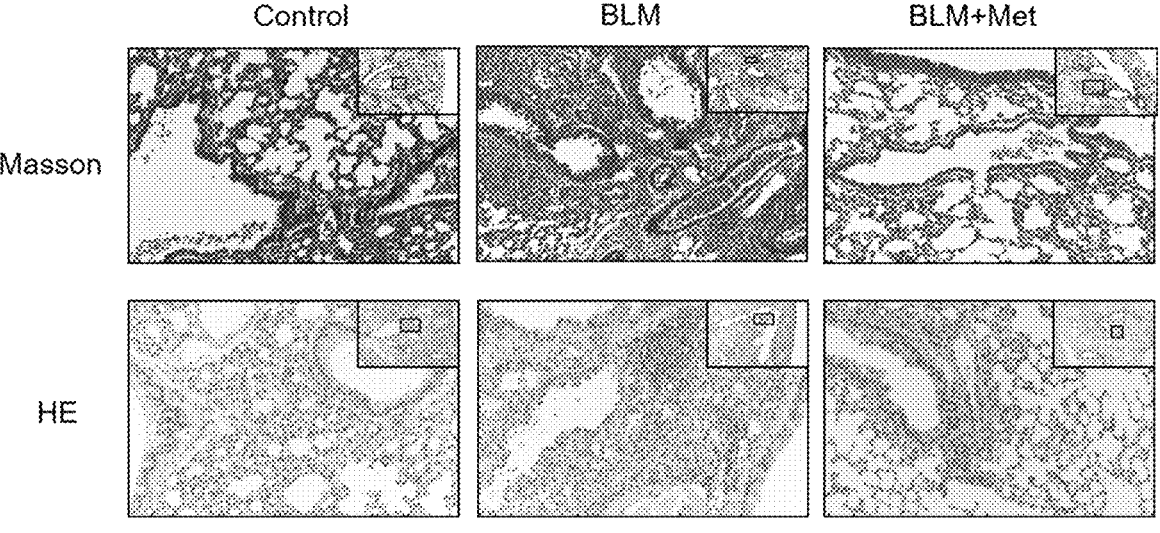
FIG. 6 shows an effect of atomized inhalation of metformin on pathological damage of pulmonary fibrosis (×200).

2) Metformin is Able to Reduce the Pathological Damage of Pulmonary Fibrosis According to Masson and HE staining in FIG. 6, compared with the Control group, the collagen fibers in BLM group are obviously increased, the degree of fibrosis is obviously aggravated, there is a large consolidation area around the bronchus, the alveolar wall is abnormally thickened and the alveolar structure is disordered. Compared with BLM group, the collagen fibers in BLM+Met group are significantly reduced, the degree of fibrosis is significantly improved, the alveolar structure is complete, the septum is normal, and there are no obvious inflammatory cells in alveolar cavity and alveolar septum.

3) Metformin Decreases the Expression Level of α-SMA

Figure 7:
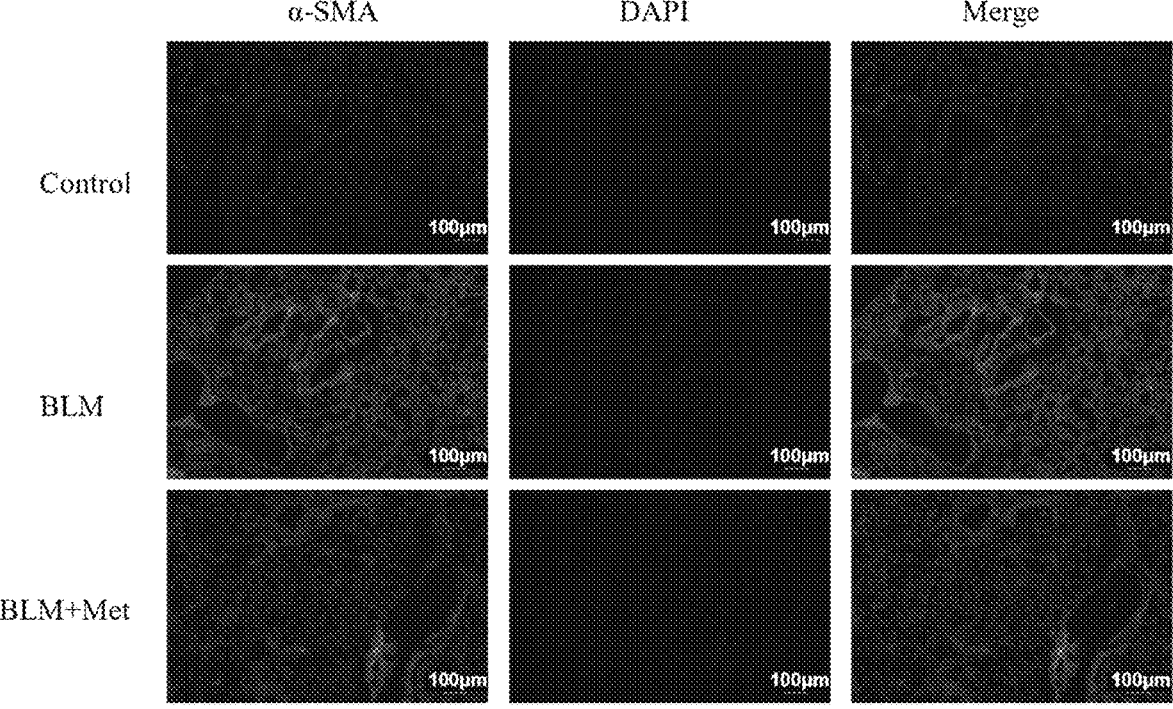
FIG. 7 shows alpha-smooth muscle actin (α-SMA) immunofluorescence (×200).

As can be seen from FIG. 7, compared with the Control group, the expression of α-SMA in BLM group is increased significantly. Compared with BLM group, the expression of α-SMA in BLM+Met group is decreased significantly.

4. Equivalent Dose Between Different Species

According to the experimental results and the conversion rules of equivalent dose between different species (as shown in table 3), the no observable adverse effect level (NOAEL) of mice is converted into the human equivalent dose HED. In other words, metformin HED (mg/kg)=NOAEL of mice/12.3=200 mg/kg/12.3=16.3 mg/kg, and HED=16.3 mg/kg× 60 kg=978 mg for an adult with a weight of 60 kg. The safety factor is 10, so the maximum recommended initial inhalation dose of metformin is 97.8 mg for the first human study.

Among them, NOAEL: no observable adverse effect level dose obtained through animal preclinical toxicology research; HED: human equivalent dose.

Therefore, according to the weight of human body, the daily inhalation dose of metformin inhalation powder is 100-4500 mg.

TABLE 3

| | | | | Conversion rules of equivalent dose between different species | | |
|---|---|---|---|---|---|---|
| | | | | | The animal dose (mg/kg) is converted into HED (mg/kg) | |
| | | Standard | Body | Standardization of body surface | | |
| Species | Standard weight (kg) | weight range (kg) | surface area (m²) | area: multiply animal dose (mg/kg) by Km | Divide the animal dose by | Or multiply the animal dose by |
| Adult | 60 | — | 1.62 | 37 | — | — |
| Children* | 20 | — | — | 25 | — | — |
| Mouse | 0.02 | 0.011-0.034 | 0.007 | 3 | 12.3 | 0.081 |
| Hamster | 0.08 | 0.047-0.157 | 0.016 | 5 | 7.4 | 0.135 |

TABLE 3-continued

| | | | | The animal dose (mg/kg) is converted into HED (mg/kg) | |
|---|---|---|---|---|---|
| | Standard | Body | Standardization of body surface | | |
| Species | Standard weight (kg) | weight range (kg) | surface area (m²) | area: multiply animal dose (mg/kg) by Km | Divide the animal dose by | Or multiply the animal dose by |
| Rat | 0.15 | 0.08-0.27 | 0.025 | 6 | 6.2 | 0.162 |
| Stoat | 0.30 | 0.16-0.54 | 0.043 | 7 | 5.3 | 0.189 |
| Guinea pig | 0.40 | 0.208-0.700 | 0.05 | 8 | 4.6 | 0.216 |
| Rabbit | 1.8 | 0.9-3.0 | 0.15 | 12 | 3.1 | 0.324 |
| Dog | 10 | 5-17 | 0.50 | 20 | 1.8 | 0.541 |
| Monkey | 3 | 1.4-4.9 | 0.25 | 12 | 3.1 | 0.324 |
| Marmoset | 0.35 | 0.14-0.72 | 0.06 | 6 | 6.2 | 0.162 |
| Squirrel monkey | 0.60 | 0.29-0.97 | 0.09 | 7 | 5.3 | 0.189 |
| Baboon | 12 | 7-23 | 0.60 | 20 | 1.8 | 0.541 |
| Pigmyhog | 20 | 10-33 | 0.74 | 27 | 1.4 | 0.730 |
| Minipig | 40 | 25-64 | 1.14 | 35 | 1.1 | 0.946 |

*The Km value of children is only for reference, and basically no healthy children become the subjects of phase II clinical trials.

To sum up, the above embodiments are only used to illustrate the technical scheme of the present application, not to limit it. Although the present application has been described by referring to some preferred embodiments of the present application, those skilled in the art should understand that various changes may be made in form and detail without departing from the spirit and scope of the present application as defined in the claims.

What is claimed is:

1. A preparation method of a metformin inhalation powder aerosol for treating idiopathic pulmonary fibrosis, comprising following steps:

S1, pretreating a metformin raw material to obtain fine powder for later use;

S2, passing the fine powder obtained in the S1 through a screen with a mesh size of 100-1000 microns by a pendular granulator at a rotating speed of 200 revolutions per minute to obtain soft particle clusters;

S3, pre-spheronizing the particle clusters in the S2 for 10-300 seconds at a vibration frequency of 100-300 hertz to obtain particle clusters;

S4, rolling the particle clusters obtained in the S3 on a granulating pan, wherein a rotation speed of the granulating pan is 5-90 revolutions per minute, an angle between the granulating pan and a horizontal plane is 0-80°, and spheronizing is carried out for 1-30 minutes to obtain spherical particle clusters; and S5, filling the spherical particle clusters obtained in the S4 into capsules by a capsule filling machine to obtain the metformin inhalation powder aerosol.

2. The preparation method according to claim 1, wherein the metformin raw material is metformin or a metformin sodium.

3. The preparation method according to claim 1, wherein D90 in the fine powder is less than 5 microns.

4. The preparation method according to claim 1, wherein the S2 further comprises an excipient, the excipient is lactose monohydrate or mannitol, the fine powder and the excipient are granulated by an oscillating granulator.

5. The preparation method according to claim 4, wherein a mass ratio of the metformin raw material to the excipient is (10-100):(1-90).

6. The preparation method according to claim 4, wherein D90 of the excipient is less than 30 microns.

7. The preparation method according to claim 1, wherein the metformin inhalation powder aerosol is administered by a dry powder inhaler, wherein the dry powder inhaler comprising: a dust-proof cover, a suction nozzle, a medicine bin, a bottom cover and two needling units, wherein the suction nozzle, the medicine bin and the bottom cover are sequentially connected, a channel is arranged on the suction nozzle, the channel has a spiral channel structure, and a grid filter screen is arranged at a bottom of the channel, the dust-proof cover is arranged on the suction nozzle, the medicine bin is provided with a medicine storage bin for placing the metformin inhalation powder aerosol, left and right sides of a lower part of the medicine bin are provided with through holes communicated with the medicine storage bin; and the two needling units are symmetrically arranged on the left and right sides of the lower part of the medicine bin, and each of the needling units comprises a button, a steel needle, a needle seat and a spring, the needle seat is arranged on an inner side of the button, an end of the steel needle is arranged on an inner side of the needle seat, an other end of the steel needle extends into corresponding one of the through holes, and the spring is sleeved on the steel needle between the needle seat and an outer wall of the medicine bin.

8. The preparation method according to claim 7, wherein the channel is a double spiral channel.

9. The preparation method according to claim 8, wherein the double spiral channel comprises fan-shaped rotating ribs and rectangular spiral ribs, and the fan-shaped rotating ribs and the rectangular spiral ribs surround an inner wall of the channel at intervals.

10. A metformin inhalation powder aerosol for treating idiopathic pulmonary fibrosis, comprising spherical particle clusters of metformin having a D90 particle size of less than 5 microns and an excipient selected from lactose monohydrate or mannitol, wherein the metformin inhalation powder aerosol is prepared by the preparation method according to claim 1.

* * * * *